(12) United States Patent
Wang et al.

(10) Patent No.: US 10,149,649 B2
(45) Date of Patent: Dec. 11, 2018

(54) METHOD FOR IDENTIFYING EXERCISE PATH, METHOD FOR SEARCHING FOR EXERCISE PATH, AND SYSTEM THEREOF

(71) Applicant: ZAN QUAN TECHNOLOGY CO., LTD, Taichung (TW)

(72) Inventors: Kai-Li Wang, Taichung (TW); Nien-En Tung, Taichung (TW); Kai-Chun Wang, Taichung (TW)

(73) Assignee: Kai-Li Wang, Taipei (TW)

( * ) Notice: Subject to any disclaimer, the term of this patent is extended or adjusted under 35 U.S.C. 154(b) by 150 days.

(21) Appl. No.: 15/186,613

(22) Filed: Jun. 20, 2016

(65) Prior Publication Data
US 2017/0164891 A1    Jun. 15, 2017

(30) Foreign Application Priority Data

Jun. 26, 2015 (TW) .............................. 104120896 A
Dec. 18, 2015 (TW) .............................. 104142671 A

(51) Int. Cl.
| | |
|---|---|
| A61B 5/00 | (2006.01) |
| A61B 90/98 | (2016.01) |
| A61B 5/024 | (2006.01) |
| A61B 5/11 | (2006.01) |
| A63B 24/00 | (2006.01) |
| G06F 19/00 | (2018.01) |
| G06K 9/00 | (2006.01) |
| G16H 40/67 | (2018.01) |

(52) U.S. Cl.
CPC ............ *A61B 5/486* (2013.01); *A61B 5/0022* (2013.01); *A61B 5/02438* (2013.01); *A61B 5/1112* (2013.01); *A61B 5/6898* (2013.01); *A61B 90/98* (2016.02); *A63B 24/0062* (2013.01); *A63B 24/0084* (2013.01); *G06F 19/00* (2013.01); *G06K 9/00342* (2013.01); *G16H 40/67* (2018.01); *A61B 5/0086* (2013.01); *A61B 2503/10* (2013.01); *A61B 2560/0252* (2013.01); *A61B 2560/0257* (2013.01); *A63B 2024/0068* (2013.01); *A63B 2220/12* (2013.01); *A63B 2220/18* (2013.01); *A63B 2220/30* (2013.01); *A63B 2220/40* (2013.01); *A63B 2220/72* (2013.01); *A63B 2220/73* (2013.01); *A63B 2220/74* (2013.01); *A63B 2220/75* (2013.01); *A63B 2220/76* (2013.01); *A63B 2225/50* (2013.01); *A63B 2230/06* (2013.01); *A63B 2230/75* (2013.01)

(58) Field of Classification Search
CPC ..... A61B 5/486; A61B 5/6898; A61B 5/1112; A61B 5/02438; A61B 5/002; A61B 90/98; A63B 24/0084; A63B 24/0062
See application file for complete search history.

(56) References Cited

U.S. PATENT DOCUMENTS

2015/0072712 A1*   3/2015   Huang .................. H04W 4/028
                                                                455/456.3

* cited by examiner

*Primary Examiner* — Toan Le
(74) *Attorney, Agent, or Firm* — Brown & Michaels, PC

(57) ABSTRACT

The present disclosure provides a method for identifying an exercise path, a method for searching for an exercise path, and a system thereof. The present disclosure can identify the forms of the exercise paths represented by exercise data and assign them with different codes. In addition, a user can search the exercise data that the user wants by using the codes, and then the exercise data can be applied onto the path on which the user desires to exercise for comparison of exercise performance. Therefore, interaction and fun in finding virtual exercise opponents can be promoted.

17 Claims, 4 Drawing Sheets

METHOD FOR IDENTIFYING EXERCISE PATH, METHOD FOR SEARCHING FOR EXERCISE PATH, AND SYSTEM THEREOF

CROSS-REFERENCE TO RELATED APPLICATIONS

This application claims priority from Taiwan patent application number 104120896, filed on Jun. 26, 2015, and Taiwan patent application number 104142671, filed on Dec. 18, 2015, their contents of which are provided herein in their entirety by reference.

BACKGROUND OF THE INVENTIVE CONCEPT

1. Field of the Invention

The present disclosure relates to methods for identifying an exercise path, and, more particularly, to a method for searching for an exercise path, and a system thereof using the method for identifying an exercise path.

2. Description of the Related Art

More and more people spend their time in exercise. Accordingly, a variety of exercise-related technologies are developed. With the rapid development of electronic products, mobile apparatuses with low-profile and compact-size dominate the market. People, when taking an exercise, can wear some exercise measurement receiving apparatuses.

However, when conventional mobile apparatuses search recorded exercise paths of exercise data of other users, the searched result matching result is not satisfied and does not meet a user's demands due to the lack of specificity of matching conditions in a program designed by an administrator. Besides, the exercise data of different exercise paths are not classified approximately, and cannot be compared with one another. Therefore, the user cannot find a competent opponent to compete with along different exercise paths.

Therefore, there is a need for a solution that addresses the aforementioned issues in the prior art.

SUMMARY OF THE INVENTIVE CONCEPT

The present general inventive concept provides a system, device, and method of monitoring the status of employees.

In view of the aforementioned shortcomings of the prior art, the present disclosure provides a method for identifying an exercise path, which may include: obtaining exercise data of a user, wherein the exercise data includes a plurality of coordinates and a plurality of time values corresponding to the coordinates; determining a form of the exercise path represented by the coordinates and the time values according to a first algorithm or a second algorithm, wherein the first algorithm is configured for determining whether the form of the exercise path is a closed path or an open path and assigning the exercise data with a first code, and the second algorithm is configured for determining whether the form of the exercise path is a closed path, an open path or a type of the closed path, and assigning the exercise data with a second code; and storing the exercise data and the first code or the second code corresponding to the exercise data in a database.

The present disclosure provides another method for searching for an exercise path, which may include: inputting at least one characteristic condition value, and searching the database of the above-mentioned method for at least one exercise data corresponding to the characteristic condition value; and applying one of the found exercise data corresponding to the characteristic condition value onto a path on which the user desires to exercise.

The present disclosure provides a system for searching for an exercise path using the above-mentioned method, which may include: a database stored with a plurality sets of the exercise data; and a mobile device, including: an applying module configured for applying at least one of the found exercise data corresponding to the characteristic condition value onto the path on which the user desires to exercise.

With the aforementioned method for identifying an exercise path and the method and system for searching for an exercise data in accordance with the present disclosure, the form of the exercise path represented by the exercise data can be determined, and different codes can be assigned to the exercise data for achieving classification of the exercise data. In addition, the present disclosure further allows the user to search for exercise data desired by the user using the characteristic condition value, and the found exercise data is then applied to the path on which the user desires to exercise, enabling comparison of the exercise performance of different individuals and adding interaction and fun into finding a virtual exercise partner.

BRIEF DESCRIPTION OF THE DRAWINGS

The present disclosure can be more fully understood by reading the following detailed description of the preferred embodiments, with reference made to the accompanying drawings, wherein.

DETAILED DESCRIPTION OF THE PREFERRED EMBODIMENTS

The present disclosure is described by the following specific embodiments. Those with ordinary skills in the arts can readily understand other advantages and functions of the present disclosure after reading the disclosure of this specification. The present disclosure may also be practiced or applied with other different implementations. Based on different contexts and applications, the various details in this specification can be modified and changed without departing from the spirit of the present disclosure.

Figure 1:
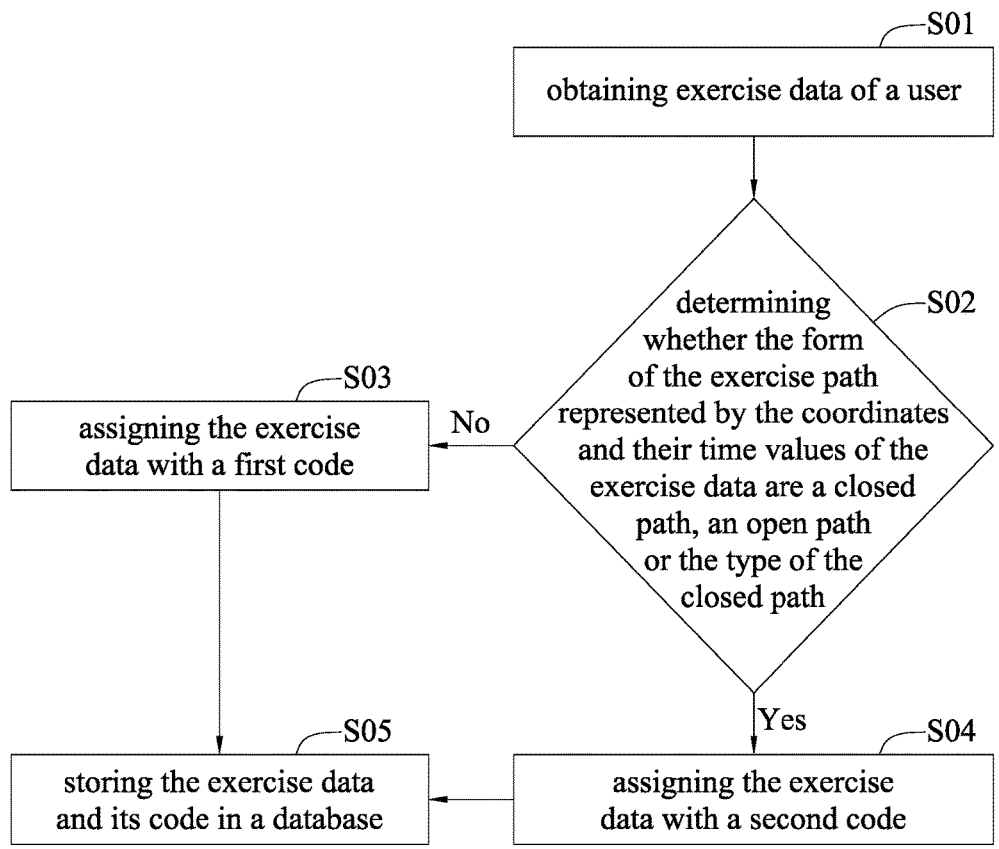
FIG. 1 is a flowchart illustrating a method for identifying an exercise path in accordance with the present disclosure.

Referring to FIG. 1, a method for identifying an exercise path in accordance with the present disclosure includes obtaining an exercise data of a user (step S01), wherein the exercise data includes a plurality of coordinates and a plurality of time values corresponding to the coordinates.

In an embodiment, the coordinates are the latitudes and longitudes coordinates of Global Positioning System (GPS). Based on the order of the time values, the coordinates are sequentially connected together to form an exercise path. Moreover, the exercise data may further include the heartbeat value, the running speed, the acceleration of the user or the calories burnt. It may also include the altitude, the slope, the barometric pressure, the temperature, the humidity, the wind direction or the wind force of the site at which the user is exercising; the present disclosure is not limited to these.

Then, the method proceeds to step S02, in which the form of the exercise path represented by the coordinates and their time values of the exercise data are determined based on a first algorithm or a second algorithm, wherein the first algorithm is used for determining whether the form of the exercise path is a closed path or an open path and assigning the exercise data with a first code accordingly; and the second algorithm is used for determining whether the form of the exercise path is a closed path or an open path or the type of the closed path and assigning the exercise data with a second code accordingly.

If the path is an open path, the method proceeds to step S03, wherein the exercise data is assigned with the first code. On the other hand, if the path is a closed path or the type of the closed path can be determined, the method proceeds to step S04, wherein the exercise data is assigned with the second code.

In an embodiment, the first algorithm sequentially converts the coordinates into a plurality of vectors based on the order of the time values. For example, ten coordinates are recorded, and two adjacent coordinates according to the order of the time values are converted into one vector. That is, ten coordinates are converted into nine vectors, but the present disclosure is not limited to converting two adjacent coordinates.

Next, the vectors are accumulated according to the order of the time values. During accumulation, if the result has ever approached or become zero, the form of the exercise path is determined as closed; otherwise, the form of the exercise path is determined as not closed.

For example, a plurality of coordinates represent the circular path of a running track. Since the running track is circular and a closed path, the starting point is also the finishing point. Therefore, in theory after the coordinates representing the circular path of the running track are converted into vectors and accumulating the vectors according to the order of the time values, the accumulation result will become zero during the accumulation process. As such, upon obtaining a zero accumulation result, the form of the exercise path of the exercise data is determined to be a closed path. As GPS itself may have some errors, the accumulation may not be zero but approaches zero. In such situation, the form of the exercise path of the exercise data is also determined to be closed path. Otherwise, the form of the exercise path of the exercise data is determined as an open path.

In an embodiment, after determining the form of the exercise path of the exercise data is a closed path, the second algorithm can be further used for determining the type of this closed path. In another embodiment, a plurality of algorithms can be used simultaneously to determine whether the form of the exercise path of the exercise data is a closed path and also the type of the closed path. In other words, there is no specific order in which the determining of the form of the exercise path and the determining of the type of closed path are implemented. The present disclosure is not limited to the order set forth in the specification.

In one embodiment, in order to determine whether the exercise path of the exercise data is a closed path and a regular path (e.g., a circular or an elliptical running track) or an open path (e.g., a straight line), the second algorithm calculates the curvature of an arc formed by any three points in the coordinates. A plurality of curvatures are obtained.

The curvature is defined as the inverse of the radius of the arc formed by any three points. In the case of a circular path, the curvatures are equal; in an elliptical path, the curvatures will form a specific curve when represented in a 2D graph (e.g., a graph of time versus curvature, a graph of distance versus curvature, a graph of an observation point sequence versus curvature; the present disclosure is not limited to these graphs). Thus, the curvatures or the specific curve are/is compared with the curvatures or the specific curve of a known exercise path to determine the type of the path.

In yet another embodiment, the second algorithm can further calculate a plurality of angles between unit vectors of the vectors. If the angles are the same or close to each other, the exercise path of the exercise data is determined as circular or straight. If the angles are different and vary by a certain amount, the form of the exercise path of the exercise data is determined as other forms (e.g., elliptical, running-track-type circular). Therefore, the variation of the angles (e.g., 2D graph) is compared with the variation of the angles in a known exercise path to determine the type of the path.

In still another embodiment, the second algorithm draws a straight line between any two coordinates in the coordinates of a closed path to form a plurality of first line segments. Among these first line segments, the longest line is selected as a neutral axis, and a plurality of straight lines are drawn between a point (preferably the middle point) on the neutral axis and the coordinates to form a plurality of second line segments. A distribution chart is plotted with the second segment number as the X axis and the length of the second segments as the Y axis. For example, the middle point of the neutral axis of a circle is the center of the circle; the lengths of the second segments are the radii of the circle; and the distribution chart plotted will show a horizontal line segment (since the radii are equal). In the case of an elliptic, the distribution chart plotted will show a curve with a particular amplitude. Thus, the distribution chart is compared against distribution charts of known exercise paths to determine the type of the closed path.

In yet another embodiment, the second algorithm may draw a plurality of triangles, each of which is formed between any one point of the coordinates and two contiguous adjacent coordinates. The areas of the triangles are summed together to give an area estimated value, which is an approximation of the area enclosed by the closed path, and the area of an elliptical running track can be obtained, for example. Moreover, the coordinates can be further sequentially converted into a plurality of vectors, and the length of the exercise path is obtained by summing the absolute values of the vectors. For example, the circumference of an elliptical running track can be obtained. As such, the area estimation and the sum of the absolute values of the vectors can be compared against the area and the sum of the absolute values of the vectors of known exercise paths to determine the type of the closed path. In other words, the areas and circumferences of the running tracks are used to determine if the running tracks are the same type (e.g., 400-meter running tracks).

In still another embodiment, the second algorithm may further form a plurality of vectors by connecting any two points in the coordinates, and then obtain a plurality of corresponding normal vectors from the vectors, and the possible type of the closed path is determined based on the intersections of the normal vectors. For example, for an elliptical running track, the normal vectors have at least two intersections; and for a circular running track, the normal vectors are expected to have just one intersection. Therefore, the number of intersections of the normal vectors and their relative locations can be compared with the number of intersections of the normal vectors and their relative locations of known exercising paths to determine the type of the closed path.

Two or more of the above calculation methods for the second algorithm can be combined to improve the accuracy in determining the type of the closed path, but the present disclosure is not limited to these combinations. If the calculations of the second algorithm returns an inconclusive result (undetermined type of closed path), the method returns to step S03, wherein the exercise data is assigned the first code.

After whether the exercise path represented by the exercise data is a closed path or the type of the path is determined, a different second code is assigned to each of the types of closed path (step S04) for differentiation. After the exercise path is assigned with a first code or a second code, regardless of the path being an open path or a closed path, the method proceeds to step S05, wherein the exercise data and its code are stored in a database.

Figure 2:
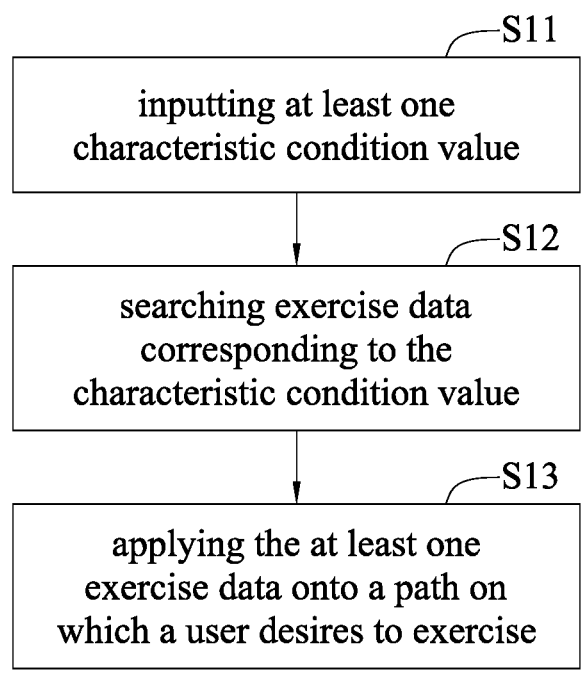
FIG. 2 is a flowchart illustrating a method for searching for an exercise path in accordance with the present disclosure.

Referring to FIG. 2, a method for searching for an exercise path is provided according to the present disclosure. First, in step S11, at least one characteristic condition value is inputted. In an embodiment, the characteristic condition value includes the exercise data or location of the user. In an embodiment, the exercise data includes the distance, the calories burnt, the running speed, the running acceleration or time, or a plurality of coordinates and a plurality of time values corresponding to the coordinates. In an embodiment, the location may be a geographical name, a street name, a place name, or the like. However, the present disclosure is not limited as such. Next, the method proceeds to step S12.

In step S12, from the database constructed in the previous method for identifying an exercise path, at least one exercise data corresponding to the characteristic condition value is searched for. Then, the method proceeds to step S13.

In step S13, at least one exercise data found corresponding to the characteristic condition value is applied onto the path along which a user wishes to exercise.

In an embodiment, the applying means converting the coordinates of at least one of the exercise data into a plurality of scalars, which are then drawn onto the path along which the user wishes to exercise according to the timing of the coordinates. As such, the user is able to observe how the other users would be doing on the exercise path on which the user wishes to exercise and compare the performance of their exercises. This comparison does not limit to the same place, thus increasing the interaction and fun of having a virtual exercise partner.

In a specific embodiment, when at least one characteristic condition value is entered, the location and the exercise data of the user are also inputted, wherein the exercise data includes a plurality of coordinates and a plurality of time values corresponding to the coordinates. Next, the form of the exercise path represented by the coordinates and their time values of the exercise data is determined using the aforementioned method for identifying an exercise path and a third code is assigned. The method for determining the form of the exercise path represented by the exercise data has already been described before, and will not be repeated again. Thereafter, the method proceeds to the next step.

In this step, a first code or a second code that is the same as the third code is searched for in the database storing exercise data each having either a first code or a second code, and an exercise data matching the location and the characteristic condition value is searched for. If an exercise data having a complete match of the location, the characteristic condition value and a first or second code (matching the third code) can be found, the exercise data is provided in a first list for the user to selection. If no exercise path having a complete match is available, the method proceeds to the next step.

In this step, the location is searched for in the database to see if there is any exercise data having either a first or second code, that is, only the location is used as the search criterion for searching for an exercise path. If an exercise data having either a first or second code associated with the location exists in the database, any exercise data having a first/second code that is similar to the third code are found and provided in a second list. In other words, other user(s) has/have already done exercise at this location and the path is already assigned a code, and thus only the code is used as the search criterion. On the other hand, if this location does not have any exercise data having a first/second code associated with it, an exercise data matching the location or the characteristic condition value is searched for in the database and provided in a third list (if any). In this case, the user is faced with a new exercise path (no previous data exists), such that search criteria other than the code are used for the search.

Regardless of whether it is the second list or the third list, after the user has selected an exercise data on the list, the exercise data is then applied to the path of the location along which the user desires to exercise. The above applying means converts the coordinates of an exercise data of the second list or the third list into a plurality of scalars and drawing the scalars onto the path of the location according to the timing of the coordinates. However, the present disclosure is not limited to this specific embodiment.

Figure 3:
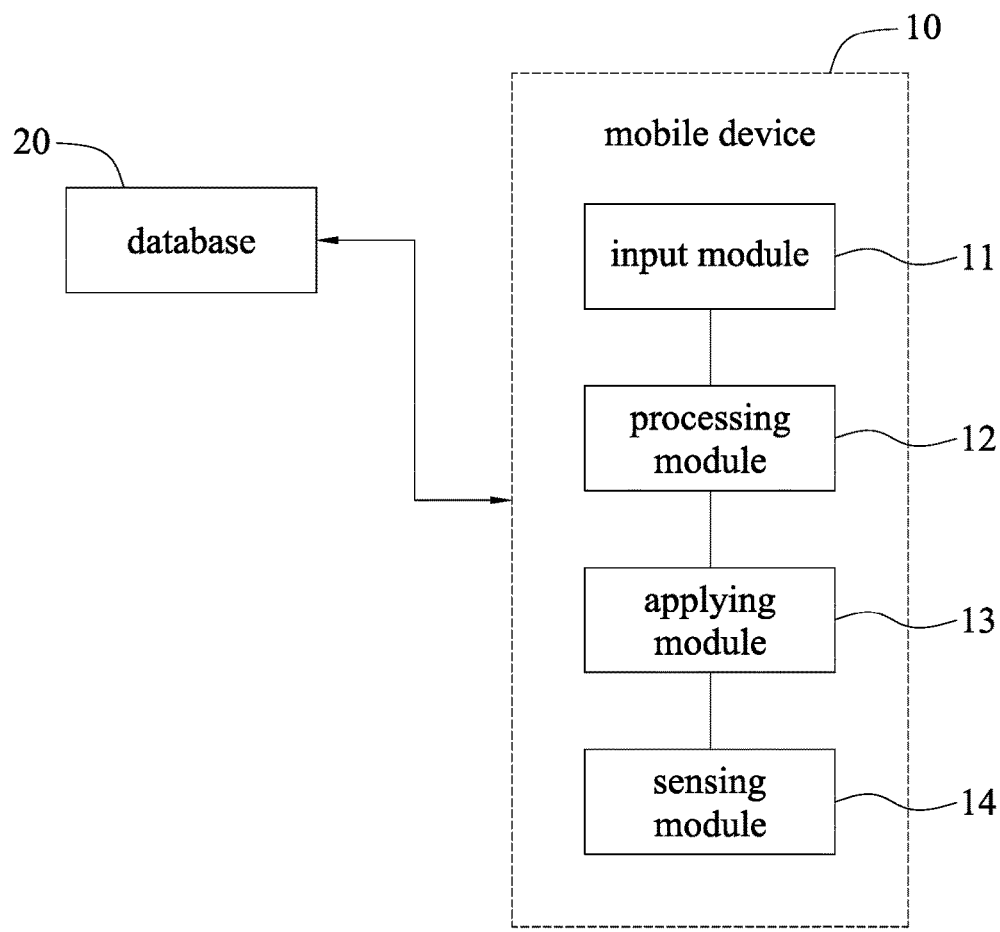
FIG. 3 is a schematic block diagram illustrating a system for searching for an exercise path in accordance with one embodiment of the present disclosure.

The present disclosure further provides a system for searching for an exercise path using the above method for searching for an exercise path. Referring to FIG. 3, the system for searching for an exercise path includes a database 20 and a mobile device 10. The database 20 stores a plurality of sets of exercise data. In an embodiment, the database 20 stores a plurality of sets of exercise data having the first code or the second code. The method for assigning the exercise data with the first code or the second code has already been described above, and will not be repeated again. The database 20 is located in the cloud server, but the present disclosure is not limited as such.

In the embodiment shown in FIG. 3, the mobile device 10 includes an input module 11, a processing module 12, an applying module 13 and a sensing module 14. In an embodiment, the mobile device 10 can be, but not limited to, a smartphone, a tablet PC or a smart wearable device (e.g., watches or glasses etc.).

The input module 11 is used for inputting at least one characteristic condition value, and for inputting search criteria such as exercise data and location of the user simultaneously. In an embodiment, the input module 11 is embodied as an input interface rendered by a software program, such as a virtual keyboard, speech input and the like.

The processing module 11 is used for searching a database in a cloud server for at least one exercise data corresponding to the characteristic condition value. In another embodiment, the processing module 12 may also determine the form of the exercise path represented by the exercise data of the user by using the algorithm written in the software program, and assign it with a third code. The specific identification method has already been described above, and will not be repeated.

The applying module 13 is used for applying one of the exercise data found corresponding to the characteristic condition value to a path on which the user wishes to exercise. In an embodiment, the applying module 13 converts a plurality of coordinates of one of the exercise data into a plurality of scalars, and drawing in time sequence the scalars on the path on which the user wishes to exercise. The applying module 13 is an algorithm written using the software program.

In another embodiment, the processing module 12 also compares the exercise data having the third code with a plurality of sets of exercise data having the first code or the second code, the location and the characteristic condition value to create a first list, a second list or a third list, allowing the user to subsequently select desired exercise data. Then, the applying module 13 applies the exercise data selected by the user onto the path on which the user desires to exercise. The processing module 12 also performs the comparison according to an algorithm written using the software program. The methods for creating the first, the second and third lists have already been described above, and will not repeated again.

The sensing module 14 is used for generating the coordinates and a plurality of time values corresponding to the coordinates included in the exercise data of the user. In an embodiment, the sensing module 14 can be a Global Positioning System (GPS) sensor, or a sensor implementing the triangulation technique in Wi-Fi base stations, mobile signal base stations or Radio Frequency Identification (RFID) technology, or the like. The latitude and longitude coordinates or relative coordinates and their corresponding time values can be recoded, such that the coordinates may be the latitude and longitude coordinates of the GPS or the relative coordinates from other positioning techniques. The time values are the time instances when the latitude and longitude coordinates or the relative coordinates are recorded, respectively. In addition, the sensing module 14 may also be other types of sensors, such as, but not limited to, a temperature sensor or a humidity sensor for sensing the ambient data surrounding the user at the time of exercising.

Figure 4:
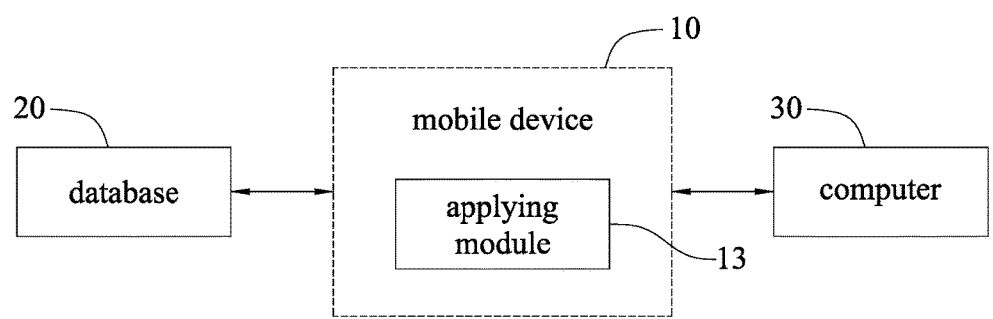
FIG. 4 is a schematic block diagram illustrating a system for searching for an exercise path in accordance with another embodiment of the present disclosure.

In another embodiment, as shown in FIG. 4, the system for searching for an exercise data further includes a computer 30, and the mobile device 10 in the system 10 includes only the applying module 13. The user enters the characteristic condition value via the computer 30, and searches for at least one exercise data corresponding to the characteristic condition value in the database 20, and then the exercise data corresponding to the characteristic condition value is/are transmitted to the mobile device 10 via a network. In this way, the mobile device 10 does not require the implementation of the input module, the processing module and the sensing module, reducing the weight of the mobile device 10 (e.g., a smart bracelet).

In conclusion, with the method for identifying an exercise path, a method and a system for searching for an exercise data in accordance with the present disclosure, the form of the exercise path represented by the exercise data can be determined, and different codes can be assigned to the exercise data for achieving classification of the exercise data. In an embodiment, the present disclosure further allows the user to search for exercise data desired by the user using the characteristic condition value, the found exercise data is then applied to the path on which the user wishes to exercise, enabling comparison of the exercise performance of different individuals, adding interaction and fun into finding a virtual exercise partner.

The above embodiments are only used to illustrate the principles of the present disclosure, and should not be construed as to limit the present disclosure in any way. The above embodiments can be modified by those with ordinary skill in the art without departing from the scope of the present disclosure as defined in the following appended claims.

What is claimed is:

1. A computer-implemented method for identifying an exercise path, comprising executing on a hardware processor of a mobile device the steps of:
   obtaining exercise data of a user, wherein the exercise data includes a plurality of coordinates and a plurality of time values corresponding to the coordinates;
   determining a form of the exercise path represented by the coordinates and the time values according to a first algorithm or a second algorithm implemented by the hardware processor, wherein the first algorithm is configured for determining whether the form of the exercise path is a closed path or an open path and assigning the exercise data with a first code, and the second algorithm is configured for determining whether the form of the exercise path is a closed path, an open path or a type of the closed path and assigning the exercise data with a second code, wherein the first algorithm converts the coordinates into a plurality of vectors according to an order of the time values, and the vectors are accumulated according to the order of the time values, and if a result during accumulation has ever approached or become zero, the form of the exercise path is determined as the closed path; otherwise, the form of the exercise path is determined as the open path; and
   storing the exercise data and the first code or the second code corresponding to the exercise data in a database implemented by the hardware processor;
   wherein the coordinates are latitude and longitude coordinates of Global Positioning System (GPS), or relative coordinates of a triangulation technique in Wi-Fi base stations, mobile signal base stations or Radio Frequency Identification (RFID) technology.

2. The method of claim 1, wherein the exercise data further includes a heartbeat value, a running speed, a running acceleration or calories burnt of the user, or an altitude, a slope, a barometric pressure, temperature, humidity, a wind direction or a wind force of a site at which the user is exercising.

3. The method of claim 1, wherein the second algorithm calculates a plurality of curvatures sequentially based on any three points in the coordinates to determine the form of the exercise path.

4. The method of claim 1, wherein the second algorithm calculates a plurality of angles between unit vectors of a plurality of vectors converted from the coordinates to determine the form of the exercise path.

5. The method of claim 1, wherein the second algorithm selects a longest line segment from line segments sequentially drawn between adjacent coordinates as a neutral axis, connects the coordinates with a chosen point on the neutral axis, and draws a distribution chart based on the length of the connected lines, and wherein the type of the closed path is determined based on the distribution chart.

6. The method of claim 1, wherein the second algorithm forms a plurality of triangular areas, each of the triangular areas is formed between any one point of the coordinates and two contiguous adjacent coordinates, and a sum of the triangular areas and a sum of absolute values of a plurality of vectors sequentially converted from the coordinates are configured for determining the type of the closed path.

7. The method of claim 1, wherein the second algorithm forms a plurality of normal vectors on respective lines formed by connecting any two points in the coordinates, and the intersections of the normal vectors are configured for determining the type of the closed path.

8. A computer-implemented method for searching for an exercise path, comprising executing on a hardware processor of a mobile device the steps of:
  inputting at least one characteristic condition value, and searching the database implemented by the hardware processor according to claim 1 for at least one exercise data corresponding to the characteristic condition value; and
  applying one of the found exercise data corresponding to the characteristic condition value onto a path implemented by the hardware processor on which the user desires to exercise.

9. The method of claim 8, wherein the characteristic condition value includes the exercise data or location of the user, and the exercise data includes a distance, calories burnt, a running speed, a running acceleration or time.

10. The method of claim 8, wherein the applying includes converting the coordinates of the one of the exercise data into a plurality of scalars, and drawing the scalars based on a time sequence onto the path on which the user desires to exercise.

11. A system for searching for an exercise path using the method of claim 8, comprising:
  the database stored with a plurality sets of the exercise data; and
  a mobile device, including:
    a hardware processor; and
    an applying module configured for applying at least one of the found exercise data corresponding to the characteristic condition value onto the path implemented by the hardware processor on which the user desires to exercise.

12. The system of claim 11, wherein the mobile device further includes an input module configured for inputting the characteristic condition value and a processing module configured for searching for the at least one exercise data corresponding to the characteristic condition value in the database.

13. The system of claim 11, further comprising a computer configured for inputting the characteristic condition value to search for the at least one exercise data corresponding to the characteristic condition value from the database and transmitting the exercise data corresponding to the characteristic condition value via a network to the mobile device.

14. The system of claim 11, wherein the database is disposed in a cloud server.

15. The system of claim 11, wherein the mobile device includes a smart phone, a tablet PC or a smart wearable device.

16. The system of claim 11, wherein the mobile device further includes a sensing module configured for generating the coordinates and the time values corresponding to the coordinates included in the exercise data of the user, and wherein the coordinates are latitude and longitude coordinates of Global Positioning System (GPS), or relative coordinates of a triangulation technique in Wi-Fi base stations, mobile signal base stations or Radio Frequency Identification (RFID) technology, and the time values are the time when the coordinates are recorded.

17. The system of claim 11, wherein the applying module converts the coordinates of the one of the exercise data into a plurality of scalars, and drawing in time sequence the scalars on the path on which the user desires to exercise.

* * * * *